United States Patent [19]
Dunn et al.

[11] Patent Number: 5,755,576
[45] Date of Patent: May 26, 1998

[54] DEVICE AND METHOD FOR TESTING DEXTERITY

[75] Inventors: William L. Dunn, Durham; Hiawatha C. Demby, Chapel Hill, both of N.C.; Michael H. Van Haaren, New Carlisle, Ohio; Abdelfatah M. Yacout, Raleigh; Mark E. Williams, Chapel Hill, both of N.C.

[73] Assignee: Quantum Research Services, Inc., Durham, N.C.

[21] Appl. No.: 551,147

[22] Filed: Oct. 31, 1995

[51] Int. Cl.$^6$ ................................................ G01R 33/20
[52] U.S. Cl. ........................... 434/258; 434/236; 273/454
[58] Field of Search .......................... 128/782; 434/258, 434/247, 351, 236; 273/445, 446, 447, 448, 454, 455, 460; 463/7, 36, 37

[56] References Cited

U.S. PATENT DOCUMENTS

| | | | |
|---|---|---|---|
| 3,913,909 | 10/1975 | Bissell | 273/1 |
| 4,457,722 | 7/1984 | Housand | 434/260 |
| 4,493,655 | 1/1985 | Groff | 434/351 |
| 4,589,849 | 5/1986 | Casey | 434/258 |
| 4,885,687 | 12/1989 | Carey | 364/413.02 |
| 5,158,303 | 10/1992 | Lat | 273/441 |
| 5,520,393 | 5/1996 | Rickey, Jr. | 434/258 |

OTHER PUBLICATIONS

Williams, Mark E. et al., "Manual Ability As A Marker of Dependency in Geriatric Women," J. Chron. Dis. 35:115–122, 1982.

Ostwald, Sharon K. et al., "Manual Dexterity as a Correlate of Dependency in the Elderly," J. Amer. Geriatrics Soc. 37:963–969, 1989.

*Primary Examiner*—Jerome Donnelly
*Attorney, Agent, or Firm*—Olive & Olive, P.A.

[57] ABSTRACT

An automated timed manual performance (TMP) system which includes a base unit having attached manual dexterity test components. Connected to the base is a reaction sensor which allows determination of the exact time of beginning and ending the manual dexterity task(s). The sensor is also connected to either a personal computer or a direct readout device. The system also optionally includes software to guide an operator through administration of a TMP test, and to display and analyze the results of the test.

20 Claims, 4 Drawing Sheets

DEVICE AND METHOD FOR TESTING DEXTERITY

BACKGROUND OF THE INVENTION

1. Field of the Invention

This invention relates to tests for timed manual performance for assessing functionality and capability.

2. Description of the Related Art

Manual tests for timed manual performance (TMP) have been used for many years to assess the functionality and capability of elderly people or others with possible diminishment of manual dexterity or cognitive function. Researchers have found that manual dexterity correlates with dependency in the elderly and the need for increased care, such as institutionalization. It has been concluded from such studies that musculoskeletal coordination, strength, vision and cognitive ability are needed to perform such everyday tasks as successfully opening and closing multiple latched doors.

For example, Williams et al. (J. Chron. Dis. 35:115–122, 1982) found that the time required to perform 27 manual skills was more closely correlated to the level of institutional support required than other variables considered such as age, education, income, medical problems, and medication. A first part of the manual assessment consisted of opening and closing a variety of fasteners (bolt latch, screen door latch, padlock, etc.) fastened to plywood doors, with timing done by a stopwatch. Participants were timed from when the researcher said "Go" until the opened door was perpendicular with the panel to which the doors were attached. A second part of the manual assessment was timing of tasks such as writing a short sentence, turning over cards, picking up various objects, and transferring objects in position.

Work by Ostwald et al. (J. Amer. Geriatrics Soc. 37:963–969, 1989) showed that manual dexterity explained 51% of the variance in residential living site of the elderly women studied. These researchers tested manual dexterity using a board with nine doors mounted with a variety of fasteners. There were 17 discrete measurements of time in the opening of nine doors and the closing of eight doors.

Dr. Mark Williams and co-workers (J. Amer. Geriatrics Soc. 42:21–27, 1994) have used a simpler apparatus to test manual dexterity in patients, comprising a box having only three doors. Researchers utilizing this simpler apparatus also utilize a stopwatch and observe the patient perform the required opening of the three doors and closing of two of the doors.

In previous manual dexterity tests, when a signal to begin is given, for example, a light going off, the patients have differing speeds of mentally processing the signal, so that they begin their physical response for the particular manual performance at different speeds. It is difficult for an observer to manually time a subject's response without including the observer's reaction time in the measurement.

Examples of patents related to manual dexterity testing and development include the patent of Bissell for an electronic game or manual dexterity testing device which has a wand or tracer for the operator to simultaneously touch a contact plate while passing the tracer over a spiral or helical conductor (U.S. Pat. No. 3,913,909). The dexterity evaluation apparatus of Casey (U.S. Pat. No. 4,589,849) provides an indication of an individual's dexterity by determining the amount of time required to assemble a circuit on a simulated electronic circuit board.

The tracking instrumentation for measuring human motor control of Carey (U.S. Pat. No. 4,885,687) has a load cell or potentiometer for converting a force or position to an electrical signal. Tests include having the subject trace a number of patterns as accurately as possible by squeezing the handgrip with the correct intensity and timing, and having the subject trace a pattern as exactly as possible by delicate adjustment of the flexion-extension position of the MP joint of the index finger.

The patent of Housand is for an educational toy for developing manual dexterity and having numerous complicated fasteners and locks (U.S. Pat. No. 4,457,722). The device of Lat (U.S. Pat. No. 5,158,303) is both for developing and testing eye-hand coordination and utilizes an electrically conductive track and a conductive loop to be moved along the conductive track.

Many of the above examples of manual dexterity tests known in the art rely on the observational skills and to some extent also on the dexterity of the researcher in beginning the timing of the test events, and analyzing when the test has been completed by the person being tested; in other tests the response is not actually timed. It is difficult for the researcher to time subparts of the response. For example, it is difficult to separate the time for the patient's hands to get to the latch of the first door versus the time it takes to open the first door.

It is therefore an object of this invention to provide a system for automated timing of manual performance.

It is a further object of this invention to provide a system which enables accurate determination of the beginning and ending of the timed manual activity(ies).

It is a further object of this invention to provide a system which allows accurate monitoring and automatic recording of patient manual performance.

The system of the invention is clinically useful in assessing function, and is predictive in nature of the subject's ability to live independently (Williams, J., Amer. Geriatric Soc. 35:761–766, 1987) and to perform desired tasks such as safely drive a car (Marottoli et al., Ann. Intern. Med. 121:842–846, 1994) or exercise proper oral hygiene (Doherty et al., Sp. Care Dentistry 14(4):144–152, 1994).

Other objects and advantages will be more fully apparent from the following disclosure and appended claims.

SUMMARY OF THE INVENTION

The automated timed manual performance (TMP) system, which will be called COGNATEMP™, comprises a preferably portable base having attached thereto a plurality of manual dexterity test components. One or more reaction sensors are connected to the base, either directly or through an interface unit. The reaction sensors allow determination of the exact time that the subject begins or completes a manual dexterity task. The reaction sensors can also be used to measure reaction time of the subject, i.e., the time from when a start signal is given until the subject initiates the task, for instance, by moving a hand or foot off the reaction sensor. The system also optionally includes software to guide an operator through administration of a TMP test, and to display and analyze the results of the test.

Other aspects and features of the invention will be more fully apparent from the following disclosure and appended claims.

3

DETAILED DESCRIPTION OF THE INVENTION AND PREFERRED EMBODIMENTS THEREOF

Figure 10:
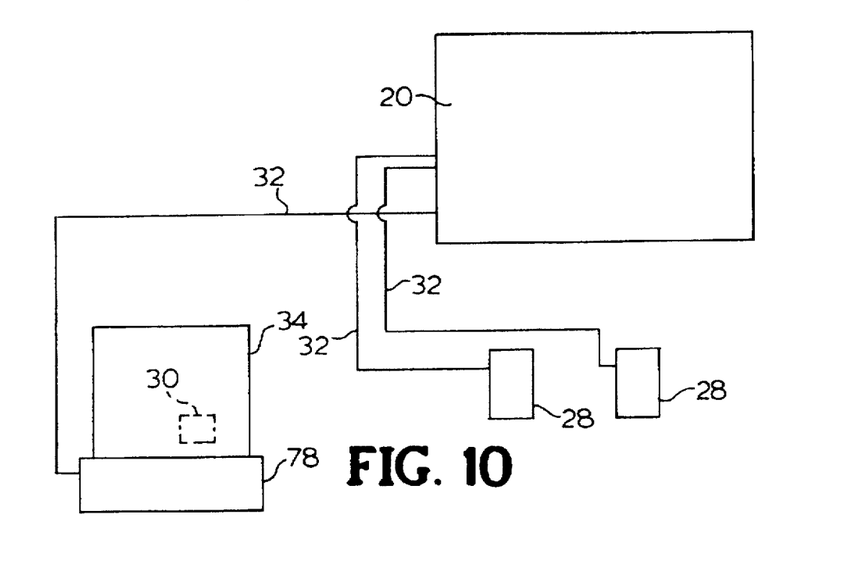
FIG. 10 is a schematic representation of the components of the system of the invention.

The present invention is for an automated system for testing timed manual performance of a person, shown schematically in FIG. 10, comprising:

(a) a base unit 20;

(b) at least one manual dexterity test component 22 attached to the base unit 20 with which manual dexterity test component 22 (FIG. 1) at least one selected task may be performed;

(c) at least one test indicator 24,26 (shown in FIGS. 3A and 3B) which electronically indicates the time when the at least one selected task is performed on the at least one manual dexterity test component 22;

(d) at least one reaction sensor 28, enabling accurate determination of the times of beginning and ending a specified manual performance test on the dexterity test component, for example, when the subject's appropriate extremity such as hand, finger, or foot leaves or returns to a known position;

(e) an electronic timer 30;

(f) electronic connectors 32 connecting the at least one reaction sensor 28 and the at least one test indicator to the electronic timer; and (g) a display system 34 for showing performance of the person.

As used herein, the term "manual dexterity test component" preferably relates to a component for testing hand coordination and movement parameters, but, in the broadest embodiment of the invention, includes any component which may be used to test performance, for example, to test various types of arm, hand, finger, foot, toe, or leg movement of various types, strength, or other parameter.

Figure 1:
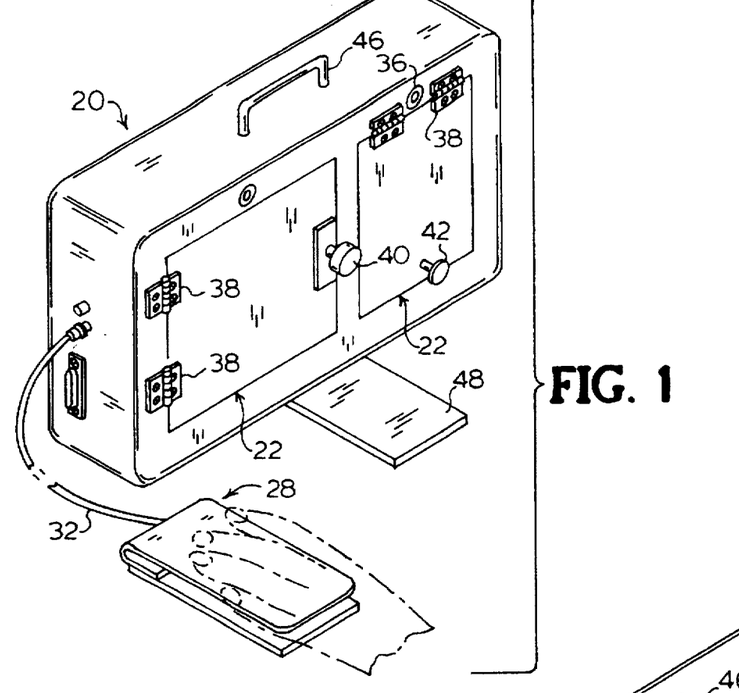
FIG. 1 is a front perspective view of a first embodiment of the automated timed manual performance system of the invention.
Figure 2:
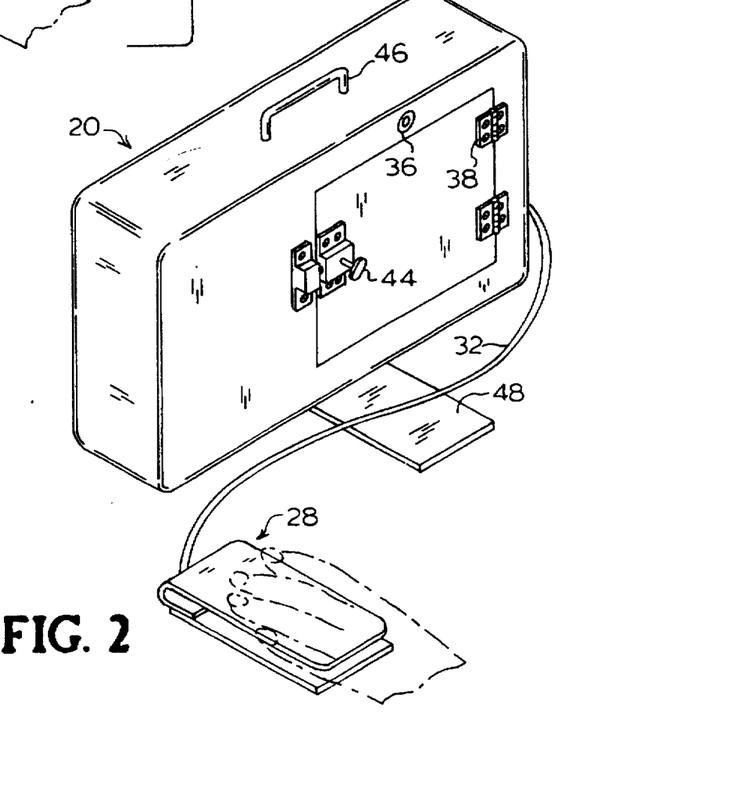
FIG. 2 is a back perspective view of the embodiment of FIG. 1.

The system also preferably comprises a beginning signal or cue device 36 (FIG. 1) attached to the base unit 20, and most preferably a beginning signal device is attached to the base unit 20 near to each manual dexterity test component 22. For example, a light may be mounted above each door as shown in FIGS. 1–2.

4

The base unit 20 may be any one of numerous designs. In the first embodiment shown in FIGS. 1–2, the base unit 20 is a box having six rectangular sides, two of which are large enough to contain latched doors, or other manual dexterity test components, for use in testing manual dexterity. Preferred base unit dimensions are about 19×11×5 inches, which allows performance of efficient, standardized dexterity testing. As shown in FIGS. 1–2, in the preferred arrangement of this embodiment, there are two doors on the front side of the base unit 20, and a single door on the back side. The base unit 20 is preferably turned around to test the subject on the door on the back side or the person may move around to the opposite side of the base unit 20. Each door is preferably about ⅞"×8.8"×½". Standard door hinges 38 (e.g., 1"×1") hold the doors to the base units. Preferably a first door has a screen door latch 40 (e.g., Grainger Part No. 1J678 (W. W. Grainger, Inc., Lincolnshire, Ill.), a second door has a simple round door knob 42 (e.g., Grainger Part No. 3J884) and a third door has a cabinet lock 44 (e.g., Grainger Part No. 4J287). Use of a variety of latches and knobs allows testing of different manual dexterity skills. The second door is preferably held shut by a door magnet (e.g., Grainger Part No. 3J957) (not shown).

A carrying handle 46 is installed on the top of the base unit 20 to aid in portability.

Figures 4, 5:
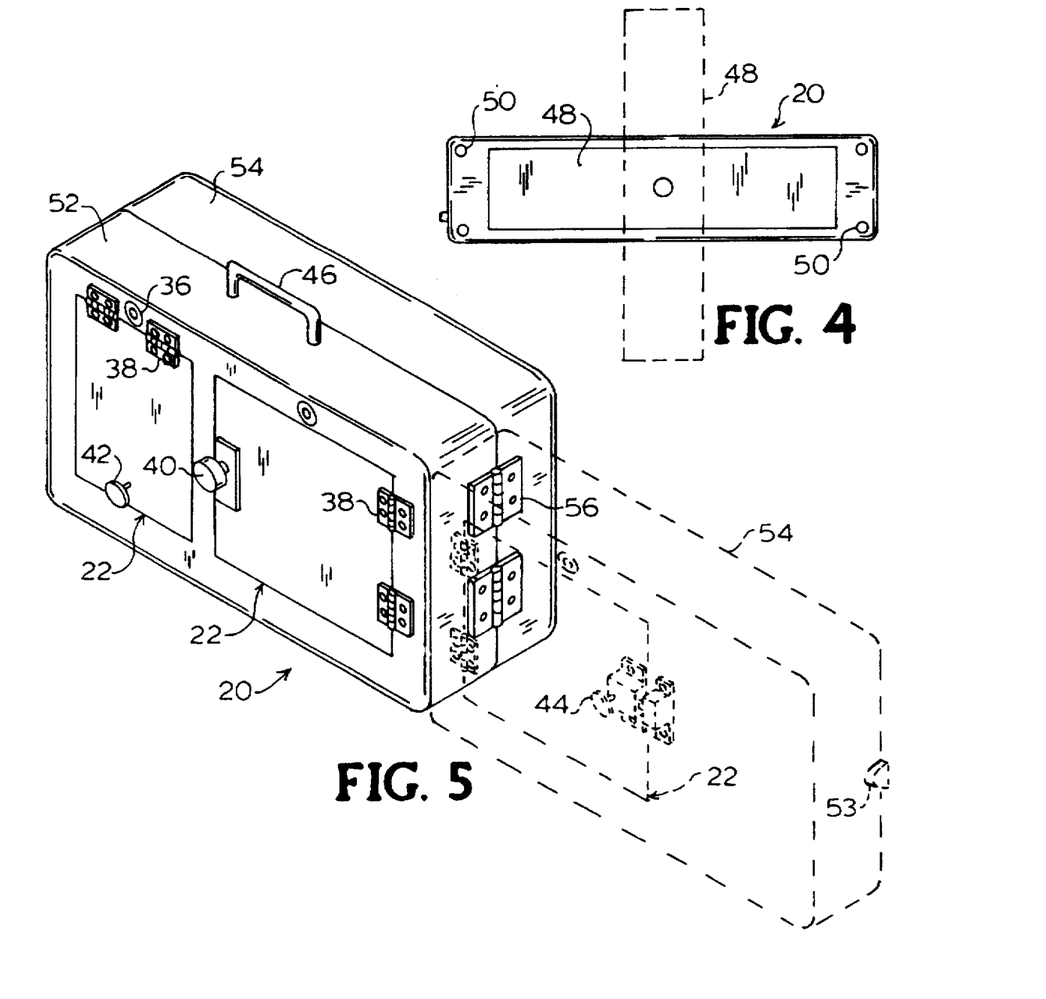
FIG. 4 is a bottom plan view of the first embodiment of the invention showing the stabilizer positions.
FIG. 5 is a perspective view of a second embodiment of the invention. The dashed lines show the open position where the back half of the base unit is pivoted about the hinged side.

To stabilize the base unit 20 of the first embodiment, it is preferred to have a stabilizer 48 pivotally attached to the bottom of the base unit 20 (FIG. 4). The stabilizer 48 may be positioned to be entirely beneath the base unit 20 when no stabilizer is needed, for example, when the base unit 20 is shipped, stored or carried, and may be positioned perpendicular to the bottom of the base unit 20 during use as shown in FIGS. 1–2 and 4. Rubber feet 50 are preferably mounted on the four corners of the base as is known in the art.

In the second embodiment of the base unit 20 of the invention, the overall base unit 20 when not in use has the same general overall appearance as in the first embodiment. The base unit structure, however, is divided as shown in FIG. 5, with a back portion 54 and a front portion 52 connected along one side by a piano hinge 56 and along the other side with a releasable latch 53, so that the back portion containing one door can be swung to be in line with the front portion containing the other two doors, and all three doors are visible to the subject at one time (the dashed lines in FIG. 5 show the back portion swung around to be in the same plane as the front of the base portion. The two portions are held together by a latch 53, for example, a chest latch when not in use or being carried (not shown).

Figures 6, 8:
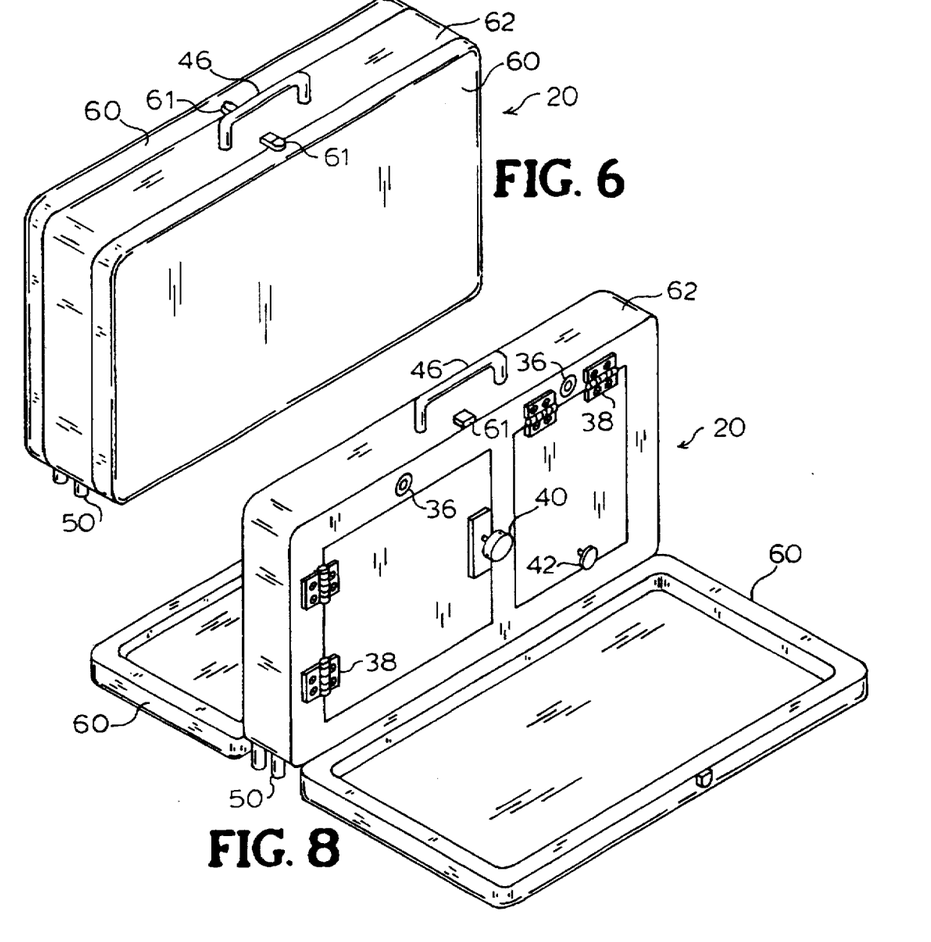
FIG. 6 is a side-front perspective view of a third embodiment of the invention in the closed position.
FIG. 8 is a perspective view of the embodiment of FIG. 6 in the open position.

In the third embodiment of the base unit 20 of the invention (FIGS. 6–8), two parallel sides 60 of the rectangular base unit fold down as shown in FIG. 8 to provide stabilizing extensions. The doors are not visible until the base unit 20 is opened because they are located on a central portion 62 of the base unit which is only exposed when the large sides are folded down. When the base unit 20 is closed it is held together with latches 61.

It is clear that within the parameters of the invention herein, the shape and form of the base unit 20 may be varied to allow testing of other types of doors or other manual dexterity tests using manual dexterity test components of any desirable size and shape, such as test components to monitor foot movement, measure leg strength, or count toe or finger taps in a pre-determined time.

Figure 3A:
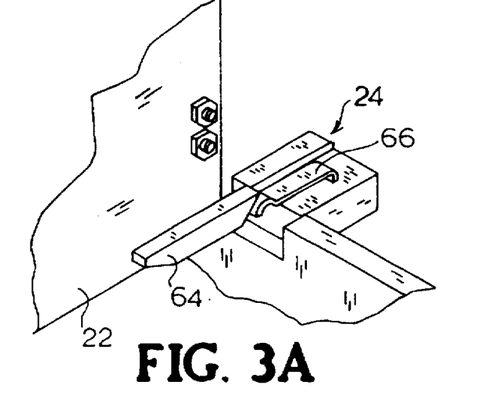
FIG. 3A is a perspective view of a door switch which may be used with the invention.

Preferably the manual dexterity test component 22 comprises at least one openable and closable door. Preferably associated with each of the preferably three doors, is a test indicator 24 (FIG. 3A) comprising an electrical switch for indicating whether the openable door is completely open or is partly closed. The structure of a preferred test indicator switch is shown in FIG. 3A. In this preferred test indicator 24, a depressor bar 64 is mounted on the door and a depressible switch mechanism 66 is mounted on the base unit 20 itself. When the door is completely closed, the depressor bar depresses the depressible switch, and it continues to do so until the door is completely open as shown in FIG. 3A. Electrical connections to the depressible switch mechanism allow detection and recordation of changes in the switch position which indicate whether the door is completely open or not.

Figure 3B:
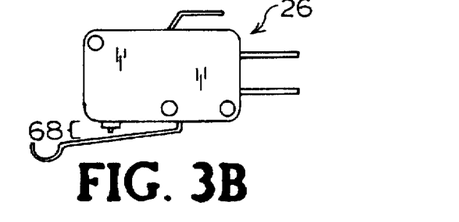
FIG. 3B is a perspective view of an electrical contact portion which may be used with the invention.

In addition, there is preferably a second test indicator 26 associated with each door which comprises an electrical contact portion 68 which provides an indication of when the door begins to be opened (no contact is made) and when the door is completely closed (contact is made). FIG. 3B shows an example of an indicator known in the art that may be used.

Figures 7, 9:
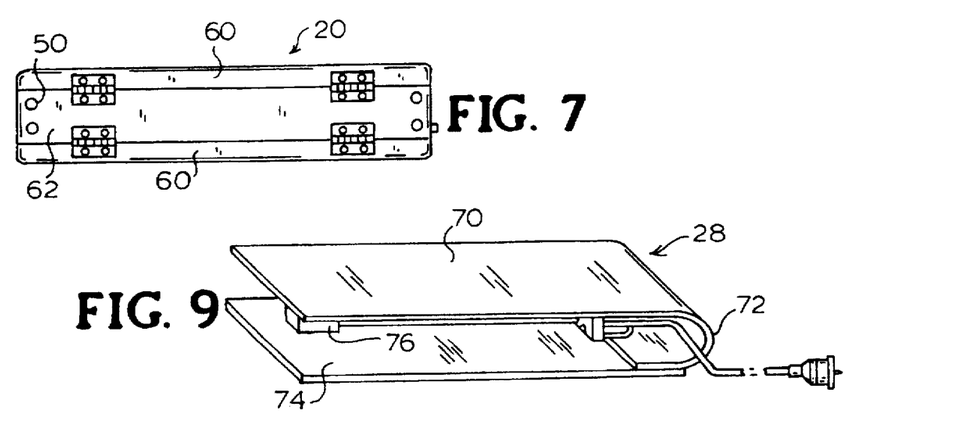
FIG. 7 is a perspective view of the bottom of the embodiment of FIG. 6.
FIG. 9 is a side perspective view of a reaction sensor which may be used with the invention.

The reaction sensor 28 allows timing of the initiation of movement by the person being tested. Preferably the reaction sensor 28 is a touch sensor (hand pad) as shown in FIG. 9. When there is one touch sensor, the person places the hand to be used in the test on the touch sensor until given the signal to begin the test. The touch sensor is sensitive to the reduction in weight when the person's hand is removed from the sensor to begin the test, and is sensitive to the increase in weight when the person's hand returns to the sensor at the beginning of the next activity. There may be two touch sensors, so that both of the person's hands may rest on a sensor until the beginning of performance of the task. The touch sensors sense removal of the hand or hands to be used in the task, and may sense which hand is removed, and sense return of the hand(s) to the sensor at the beginning of the next activity.

The structure of a preferred hand pad is shown in FIG. 9. An upper plastic piece 70 having a rear curved edge 72 is permanently affixed, for example, by glue, to a lower flat piece 74 of plastic so that the unattached ends of the two pieces are about 0.5 inch apart when there is no external pressure on them. These two pieces of plastic act as a spring against the downward force of the pad when a person's hand is resting on the pad. A microswitch 76 (e.g., 1 mm Tact, Digi-Key Corporation, Thief River Falls, Minn., Part No. P8044SCT-ND) is mounted between the two halves of the shell. When the pad is depressed, a button (not shown), for example, of hard rubber, mounted on the underside of the top shell depresses and closes the switch, as is known in the art, which is detected and recorded by the system using the connectors. A tension apparatus, such as a simple spring, may be incorporated to adjust sensitivity of the pad.

The electronic timer 30 is preferably a programmed portion of a personal computer 78, as discussed in more detail below, or a specially designed dedicated electronic circuit incorporating one more timer chips or microprocessor chips.

Figure 11:
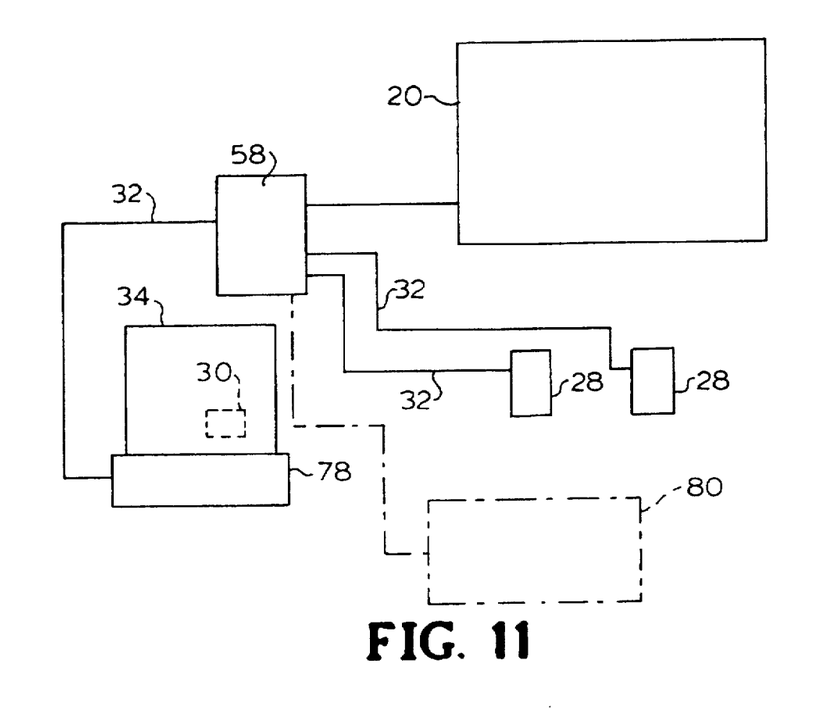
FIG. 11 is a schematic representation of an alternative configuration of the system in which an interface unit is employed.

The electronic connectors 32 may be standard electrical cables and/or wireless connections, such as electromagnetic transmitters and receivers. The connectors extending between the touch pads (hand pads) and the base unit 20 are preferably RG 174/U cable and BNC (bayonet coaxial-cable) connectors. The computer 78 is connected via a printer cable to a standard 25-pin connector (DB-25 printer cable; Newark Electronics, Chicago, Ill., Part No. 87N486) mounted on the base unit 20 or on a separate interface unit 58 (FIG. 11). The following wiring logic discussion is based on a numbering of the switches as follows: switches 1 and 2 indicate whether door 1 is closed, partially open, or fully open; switch 3 indicates whether door 2 is closed or open; and switches 4 and 5 indicate whether door 3 is closed, partially open or fully open.

An example of wiring logic to the printer connector pins for the embodiments discussed in detail herein which provides effective test administration is as follows: (pins not listed are not used): pin #2: connected to switch 2 (input to base unit from timer); pin #3: connected to switch 1 (input); pin #4: connected to switch 3 (input); pin #5: connected to switch 5 (input); pin #6: connected to switch 4 (input); pin #7: connected to touch pads in series (input); pin #8: connected to LEDs 1 and 3 (input); pin #9: connected to LED 2 (input); pin #10: status of door 1 (output to timer from base unit); pin #11: status of door 2 (output); pin #12: status of door 3 (output); pin #13: status of touch pads (output); pin #25: ground (common).

When the electronic timer (discussed below) is set at door 1, it uses pins 2 and 3 to send voltages to switches 1 and 2. When door 1 is closed, switch 1 is closed and switch 2 is open, and pin 10 transfers the signal back to the timer indicating door 1 is closed. The tester hits a key on the keyboard sending a signal to pin 8 which illuminates lights 1 and 3 (which are on opposite sides of the box (in the first embodiment of the base unit), which starts timing. The subject should begin the action of opening either door 1 or door 3, whichever is on the side where the subject is. When both the subject's hands are on the touch pads, the microswitches on both touch pads are closed and the timer voltage sent on pin 7 results in a signal back to the timer on pin 13. When either hand is lifted off the touch pad, the corresponding switch on that touch pad opens and the signal from pin 13 stops. The timer senses this and marks the reaction time. When the subject opens door 1 a small amount, switch 1 is opened, which stops the signal on pin 10. This is sensed by the timer, which then marks the initiation time. When the subject opens the door all the way, switch 2 is closed, which restarts the signal on pin 10. The timer senses this and marks the completion time for the door opening process. An analogous sequence is used for door 3. Door 2 has only one switch, which is used to indicate when the door is fully open.

The highly precise electronic timing in using the device of the invention is achieved as follows. Some currently available personal computer (PC) hardware (for example, a Toshiba Satellite 1960CS2 computer) can signal the central processing unit (CPU) of the computer via an interrupt mechanism which essentially draws the attention of the CPU by suspending the current execution, and jumping to a predefined routine known as the interrupt handler, when it acknowledges an interrupt. In such computers, each of the PCT interrupt lines has a handler, and the handler addresses of each are stored in the PCT memory. In the PC-compatible (PC-AT, PC-XT, and above to the Pentium computers), there is a timer called the 8253 timer, in which channel 0 is connected to the Interrupt Request line 0 (IRQ0) line, and can be used to generate a level 0 interrupt (type code 08H).

The normal Basic Input/Output System (BIOS) operates at 55 millisecond (msec) increments, which is equivalent to causing an interrupt once every 65,636 clock cycles. In the invention, the least significant bit (LSB) of Latch 0 (port 40H) is programmed to 00H and the most-significant bit to 10H, which sets the counter to 4,096, which causes an interrupt every 4,096 cycles. At 0.0008381 msec per cycle, the timing error of the invention timing system is less than or equal to 3.4328433262 msec. Therefore, in the invention, the personal computer (PC) 8253 timer chip channel 0 BIOS interrupt handler is replaced by a new timer (clock) routine as a new handler, enabling a clock "tick" interrupt every 4,096 clock cycles, which is equivalent to 3.4328433262 msec per tick. Replacing the BIOS interrupt as described during execution of software run during the testing of a subject allows generation of an interrupt at a faster rate, maintenance of the program clock automatically by the CPU, and avoidance of overhead associated with calls to the BIOS routines.

The timer is therefore installed by: first, retrieving and storing the address of the current interrupt handler (this is restored when the software is terminated); second, installing the above-described timer (clock) routine as the new handler; third, programming Latch 0's (port 40H) LSB to 00H and most-significant bit to 10H, thus setting the counter to 4,096 cycles; and fourth, redirecting every 16th interrupt to the old interrupt vector thereby maintaining the standard clock. The timer accumulates the clock ticks into a global variable. Whenever the time is needed, the number of clock ticks since the last initialization is multiplied by 3.4328433262 msec/tick to obtain the time.

The display system may be an electronic display device, such as a computer monitor, or a direct readout device such as a light emitting diode (LED) display device, or a liquid crystal display (LCD) module. The preferred display for a computerbased timer is the computer's cathode ray tube (CRT) monitor, which can display text, including numbers, and graphics. A simple display for use with a specially designed electronic circuit timer is a standard LED display device which displays a series of numbers.

Specialized computer software enables the most efficient performance of testing using the system of the invention. The software facilitates the measurement and administration of the TMP test. Preferably, the software includes a simulation mode to allow the operator to test the system prior to performing actual subject tests. For actual testing, a subject's name, address, and other personal information are stored along with a database of vital signs and TMP test results for that subject.

In addition, the software provides major utilities and services such as file management, time measurement (discussed above), instructions and help information, and printing functions to output comprehensive or partial TMP test data or vital information data. Preferably special functions are also included, such as a toggle switch to change between metric and English units, the capability of updating personal information, the ability to display information, and the ability to convert information to a spreadsheet form.

When the test is to be taken, the software provides instruction for taking the TMP test, and guides the operator through the test administration. When three different doors and latches are used in the test, the time it takes to both open and close the door is measured to a resolution of about 3.4328433262 msecs. An audible and optical signal is given when the test has begun, and the time it takes the subject to react (e.g., move the hand off the touch pad) is measured. For doors 1 and 3, the next measured increment is the time it takes the subject to begin to open or close the prescribed door. For all three doors, the time taken to complete the operation (e.g., fully open the door) is measured. The individual time intervals and their sum are recorded and displayed on the computer monitor for each door operation. A typical TMP evaluation screen shows the name of the subject, the date, the time to perform each portion of each task next to a depiction representing the task, for example, a line drawing of the particular door, and the total time for each task. The software checks to make sure a valid test was performed by looking at the interval time values and the operator is notified if a time measurement problem is suspected. Comments on the performance of the test can be made by the operator, and are recorded with each record. Once a test has been completed and the record stored, no further changes can be made to that record, except for deleting it, to ensure that subject records are not inadvertently modified, and that they remain accurate.

There may also be a subject information update screen in which subject personal and vital information is entered for storage in the file. The vital sign information cannot be changed once the record is entered, just as with TMP test data. When the record that may be edited (e.g., address) is edited, the date of entry is automatically entered.

A third screen is a results summary screen which summarizes the TMP test data and overall results. The operator can page through it to view prior test results.

The invention also includes methods of use of the automated system of the invention to test manual performance of a person. In the preferred embodiments of the invention where the reaction sensor 28 comprises touch sensors for use with the hand, the hand or hands of the person are placed on one or two reaction sensors, respectively. The person is instructed to perform the one or more manual dexterity tasks when the person is presented with a selected signal. The person's performance is determined from information received by the display system from the electronic timer and displayed on the display system. An example of a test protocol used with prior art devices, and which may be adapted for use with the system of the invention by including reference to the touch sensors and to the signal to begin, is taken from an article by Williams, M. E. (Identifying the Older Person Likely to Required Long-Term Care Services, J. Am. Geriatrics Soc. 35:761–766, 1987). In this example, the person administering the test says:

"This is door number__. It is fastened by a__. It is opened in this manner. (Demonstration of how fasteners are undone and how door opens.) Do you have any questions about how to open door number__? Place your hands on the table please. When I say 'go', open door number__. Ready? Go." The timing began from the work "go" and lasted until the opened door was perpendicular to the front of the panel. A similar protocol was used to time the closing of the fasteners.

Following is a summary of how the system of the invention may be set up and used. For the standard size automated system of the invention, an area of about 2×2 feet or greater is recommended to allow enough space to set up and operate the system. One or two touch pads, depending on the preference of the tester, are connected to the base unit 20 or an interface device 58. A foot, leg or toe test unit 80 may be similarly connected. Preferably, the touch pads are connected to the base unit 20 or interface device 58, using BNC ¼ turn connectors placed into BNC jacks located on one end of the base unit 20 or interface device 58, as are known in the art, and the computer cable is connected to the base unit 20 or interface device 58. If the base unit 20 has a stabilizer 48, the stabilizer 48 is positioned 90° to the long axis of the base unit. The base unit can be turned to allow access to the back side during administration of the testing.

After the apparatus is set up, the tester opens the software which has been installed in the computer, and uses it to open a subject record. The tester uses function keys to select the door to be opened, and demonstrates the opening of that door to the subject. The tester then requests that the subject place one hand on each touch pad, or the hand the subject will use, if only one touch pad is being used.

To begin the test, the tester uses a function key to ready the system so that when any key is hit on the keyboard, a signal is sent through one of the printer cable wires from the computer 78 to the base unit 20. When a key is hit, the computer 78 begins timing, a beep sounds from the internal computer speaker, and a signal is sent to the base unit 20 which causes the light near the selected door to be illuminated. The subject responds to either the tone or the light or both and opens the door.

A series of signals is sent back to the computer 78 through the printer cable as the microswitch on the touch pad is opened (when the subject's hand leaves one of the touch pads), and snap-action micro-switches mounted near the door change state due to the movement of the door. These signals are used to measure the following times: (a) reaction time, from the start signal until the subject's hand is lifted off the touch pad; (b) initiation time, from the time the subject's hand is lifted off the touch pad until the latch on the door is opened and the door is just slightly opened (on a door with a knob only and no latch, the computer does not measure or record this time); and (c) completion time, from the time the door is slightly opened until it is opened so that it is perpendicular to the front of the base unit 20.

Next the tester demonstrates how to close the door, and goes through a similar procedure to time the subject in the closing operation, except for the door with a simple round knob and no latch for which no closing time is measured (door 2 in the discussion above). On this door, the subject lifts the door to a perpendicular position for the opening test and timing stops, and then simply lowers to its original position, and the software does not record the initiation time or closing time on this simple door.

The tester uses function keys to cycle through the doors and the opening and closing operations. The software preferably used in the invention is programmed so that the start signal is sent to the appropriate pin to turn on the appropriate light indicating the selected door for the next test. At any time during the test, the tester may reselect an operation (opening or closing any door) to repeat that portion of the test. After all desired tests are complete, the tester may close the record.

Information obtained from this analysis may be used to provide counsel to family, institutions or concerned others regarding the person.

Although it may be generally preferred to conduct testing in person, it is also possible to perform testing according to the method of the invention when the person being tested is at a separate location from a location of the observer or test administrator. In such instances, the instructions for administering the testing, and results of the testing are transmitted over a telecommunications network, such as a digital fiber-optic cable, as is known in the art.

While the invention has been described with reference to specific embodiments thereof, it will be appreciated that numerous variations, modifications, and embodiments are possible, and accordingly, all such variations, modifications, and embodiments are to be regarded as being within the spirit and scope of the invention.

What is claimed is:

1. An automated electrically operated medical testing system by means of which a test-giver can test an individual test-taker's ability to execute simple manual dexterity tests when the test-taker is suspected of having declining functionality, comprising:

(a) a base unit;
   (b) at least one manual dexterity test component attached to the base unit and characterized by providing at least one selected manual dexterity task to be performed by a test-taker;
   (c) a signaling assembly including at least one signal device mounted on said base unit and productive when energized of producing a first signal perceptible by said test-taker and means connected to said signal device enabling a test-giver to activate said signal device and thereby provide said first signal as a command to said test-taker to initiate said at least one manual dexterity task;
   (d) a reaction assembly including at least one reaction sensor comprising at least one hand-touch pad for receiving at least one hand of said test-taker at the beginning of a said test and means associated with at least one said hand-touch pad responsive to said test-taker's hand being removed from said hand-touch pad for providing a second signal corresponding to the test-taker's response to said signal device command;
   (e) at least one test indicator connected to said at least one manual dexterity component and productive of a third signal responsive to said test-taker's positioning of said component and corresponding to the time when the at least one selected manual dexterity task has been completed;
   (f) a timer;
   (g) a display device; and
   (h) a processor connected to said signaling assembly, said reaction assembly, said at least one said test indicator, said timer and said display device, said processor being operative in response to said first, second and third signals to display the time said signal device is activated, the time at least one said hand-touch pad indicates said test-taker has responded to said signal device command, and the time said test indicator indicates said manual dexterity task is complete, thereby allowing the test-giver to determine the test-taker's ability to respond to said command and execute said task.

2. A system as claimed in claim 1, wherein said manual dexterity test component comprises a first openable and closable door, said test indicator comprises an on-off switching device associated with said first door and activated in response to performance of said task to produce said third signal as one of a first set of signals the first of which corresponds to said first door being partially opened, and the second of which corresponds to said first door being fully opened.

3. A system as claimed in claim 2, wherein said first door includes a door handle used in performing said task.

4. A system as claimed in claim 3, including a second openable and closable door operable as a said manual dexterity test component and a test indicator comprising an on-off switching device associated with said second door and activated in response to performance of a said manual dexterity task utilizing said second door to produce a signal corresponding to said second door being fully opened.

5. A system as claimed in claim 4, wherein said second door includes a door knob used in performing a said task by means of said second door.

6. A system according to claim 5, including a third openable and closable door operable as a said manual dexterity component, and a test indicator comprises an on-off switching device associated with said third door and activated in response to performance of a said manual texterity task utilizing said third door to produce a second set of signals the first one of which set corresponds to said third door being partially opened, and the second one of which set corresponds to said third door being fully open.

7. A system as claimed in claim 6, wherein said third door includes a door latch used in performing a said task by means of said third door.

8. A system as claimed in claim 7, wherein said first door opens in a first plane, said second door opens in a second plane perpendicular to said first plane, and said third door opens in a third plane parallel to said first plane.

9. A method for testing a test-taker's ability to execute manual dexterity tasks when the test-taker is suspected of having declining functionality, comprising:
  (a) establishing an automated electrically operated medical testing system by means of which a test-giver can test an individual test-taker's ability to execute manual dexterity tests, comprising:
    (i) a base unit;
    (ii) at least one manual dexterity test component attached to the base unit and characterized by providing at least one selected manual dexterity task to be performed by a test-taker;
    (iii) a signaling assembly including at least one signal device mounted on said base unit and productive when energized of producing a first signal perceptible by said test-taker and means connected to said signal device enabling a test-giver to activate said signal device and thereby provide said first signal as a command to said test-taker to initiate said at least one manual dexterity task;
    (iv) a reaction assembly including at least one reaction sensor comprising at least one hand-touch pad for receiving at least one hand of said test-taker at the beginning of a said test and means associated with at least one said hand-touch pad responsive to said test-taker's hand being removed from said hand-touch pad for providing a second signal corresponding to the test-taker's response to said signal device command;
    (v) at least one test indicator connected to said at least one manual dexterity component and productive of a third signal responsive to said test-taker's positioning of said component and corresponding to the time when the at least one selected manual dexterity task has been completed;
    (vi) a timer;
    (vii) a display device; and
    (viii) a processor connected to said signaling assembly, said reaction assembly, said at least one said test indicator, said timer and said display device, said processor being operative in response to said first, second and third signals to display the time said signal device is activated, the time at least one said hand-touch pad indicates said test-taker has responded to said signal device command, and the time said test indicator indicates said manual dexterity task is complete, thereby allowing the test-giver to determine the test-taker's ability to respond to said command and execute said task;
  (b) selecting a test-taker and a test-giver;
  (c) determining one or more manual dexterity tasks for the test-taker to perform on said system;
  (d) causing said test-taker to place one of the said test-taker's hands on at least one said hand-touch pad;
  (e) causing said test-giver to energize said signal device to produce said first signal as said command;
  (f) determining the time when said signal device was activated and the times when one or more of said manual dexterity tasks were completed; and
  (g) displaying the time when said signal device was activated, the time the at least one said touch pad indicates said test-taker responded to said signal device command, and the time when one or more said manual dexterity tasks were completed, thereby allowing the test-giver to determine a test-taker's ability to respond to said signal device command and to execute one or more of said manual dexterity tasks for the purpose of medical testing and treating of patients with declining functionality.

10. A method as claimed in claim 9, wherein establishing said system includes establishing said component as a first door and causing said test-taker to perform at least one of said tasks by partially opening said first door, and fully opening said first door.

11. A method as claimed in claim 10, wherein establishing said system includes the additional step of causing said test-taker to perform at least one of said tasks by closing said first door from a fully open position.

12. A method as claimed in claim 11, wherein opening said first door is accomplished in a first plane.

13. A method as claimed in claim 12, wherein establishing said system includes establishing a pair of said components comprising first and second doors and said one or more manual dexterity tasks comprises opening said second door.

14. A method as claimed in claim 13, wherein opening said second door is accomplished in a second plane perpendicular to said first plane.

15. A method as claimed in claim 14, wherein establishing said system includes establishing a said component as a third said door and said one or more manual dexterity tasks comprises partially opening said third door, and fully opening said third door.

16. A method as claimed in claim 15, wherein establishing said system includes establishing said component as a third door and causing said test-taker to exercise at least one of said tasks by closing said third door from a fully open position.

17. A method as claimed in claim 16, wherein opening said third door is accomplished in a plane parallel to said first plane.

18. A system as claimed in claim 2, wherein the third of which first set of signals is a third signal which corresponds to said first door being fully closed from a fully open position.

19. A system as claimed in claim 6, wherein the third of which second set of signals is a third signal which corresponds to said third door being fully closed from a fully open position.

20. A method as claimed in claim 18, wherein said one or more manual dexterity tasks comprises the task of removing a hand of said test-taker from at least one said hand-touch pad in response to said signal device command to produce said third signal as one of a set of signals one of which corresponds to said first door being fully closed from a fully open position.

* * * * *

UNITED STATES PATENT AND TRADEMARK OFFICE
CERTIFICATE OF CORRECTION

PATENT NO. : 5,755,576
DATED      : May 26, 1998
INVENTOR(S) : William L. Dunn et al.

It is certified that error appears in the above-indentified patent and that said Letters Patent is hereby corrected as shown below:

Column 3, line 3, correct "perspective" to read --an elevation--
Column 3, line 14, correct "perspective" to read --bottom plan--
Column 4, line 14, correct "7/8" to read --7.8--
Column 4, line 46, correct "portion." to read --portion).--
Column 5, line 3, after "switch" insert --24--
Column 5, line 3, after "indicator" insert --switch--
Column 5, line 55, after "one" insert --or--
Column 8, line 41, "The timing" should be at left margin
Column 12, line 54, correct "claim 18" to read --claim 11--

Signed and Sealed this

First Day of September, 1998

Attest:

BRUCE LEHMAN

*Attesting Officer*    *Commissioner of Patents and Trademarks*